US00PP22427P2

(12) United States Plant Patent
Egger

(10) Patent No.: US PP22,427 P2
(45) Date of Patent: Dec. 27, 2011

(54) *HEUCHERELLA* PLANT NAMED 'SOLAR POWER'

(50) Latin Name: *Heucherella* hybrid
Varietal Denomination: Solar Power

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/806,901

(22) Filed: Aug. 23, 2010

(51) Int. Cl.
*A01H 5/00* (2006.01)
(52) U.S. Cl. ..... Plt./441
(58) Field of Classification Search ..... Plt./441
See application file for complete search history.

*Primary Examiner* — Annette Para
(74) *Attorney, Agent, or Firm* — Klarquist Sparkman, LLP

(57) ABSTRACT

A new and distinct *Heucherella* plant substantially as shown and described, characterized by large, yellow to lime palmately lobed leaves, a red splatter pattern in the middle of the leaf lobes, a mounding plant habit, and excellent vigor. *Heucherella* 'Solar Power' grows equally well in full sun or filtered shade in the Pacific Northwest.

1 Drawing Sheet

Botanical denomination: *Heucherella* hybrid.

Variety designation: 'Solar Power'.

The present invention relates to a new and distinct cultivar of *Heucherella* and given the cultivar name of 'Solar Power'. *Heucherella* is in the family Saxifragaceae. *Heucherella* 'Solar Power' originated from a controlled cross between *Heuchera* 909-2 (a proprietary unreleased *Heuchera villosa* hybrid), as the seed parent, and massed selected proprietary *Tiarella*, as the pollen parent.

Compared to the seed parent *Heuchera* 909-2, the new variety has yellow to lime green colored leaves rather than red brown.

Compared to *Heucherella* 'Alabama Sunrise' (U.S. Plant Pat. No. 19,611), the new variety has leaves that are less lobed and are marked with a splatter pattern rather than a strong red pattern along the veins.

This new *Heucherella* is distinguished by:

1. large, yellow to lime palmately lobed leaves,
2. a red splatter pattern in the middle of the leaf lobes
3. a mounding plant habit,
4. grows equally well in full sun or filtered shade in the Pacific Northwest,
5. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one-year-old *Heucherella* 'Solar Power' in bloom, growing in the ground in full sun in the trial field in July in Canby, Oreg.

FIG. 2 shows the foliage color of a one and a half year old *Heucherella* 'Solar Power' grown in the shade in late summer in Canby, Oreg.

DETAILED PLANT DESCRIPTION

The following is a detailed description of the new *Heucherella* cultivar based on observations of a two-year-old specimens growing in the ground in the garden in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—25 cm tall from top of the foliage to the ground and 50 cm wide.
*Habit.*—Mounding.
*Vigor.*—Excellent.
*Roots.*—Fibrous, freely branching, fine, and white in color.

Leaf:

*Type.*—Simple.
*Arrangement.*—Rosette.
*Shape.*—Ovate.
*Lobing/division.*—5 to 7 palmate lobes with the terminal the longest, each with shallow secondary lobes.
*Venation.*—Palmate.
*Margins.*—Crenate.
*Apex.*—Mucronulate.
*Base.*—Cordate, sometimes overlapping.
*Blade size.*—Grows to 10 cm long and 9 cm wide.
*Surface texture.*—Glandular both surfaces.
*Petiole description.*—Grows to 30 cm long and 3 mm wide, glandular hairs, Yellow Green 154C.
*Leaf color.*—Spring topside Yellow 11A in high light and Yellow Green 154B in low light with splatter pattern Greyed Orange 176B, bottom side Yellow 11B and Yellow Green 154C with splatter pattern Greyed Purple 187B; summer topside Yellow Green 144B to 144C with the splatter pattern Greyed Purple 187B.

Inflorescence:

*Size.*—2.5 cm wide and 9 cm long.

*Type.*—Raceme.

*Number of flowers per raceme.*—About 50.

*Number of racemes.*—10.

*Peduncle.*—Grows to 49 cm tall, 3 mm wide at base, Yellow Green 154C, glandular hairs, no cauline leaves.

*Pedicel.*—Grows to 12 mm long, with glandular hairs, Greyed Red 182B.

*Bloom period.*—April to July in Canby, Oreg.

Flower bud:

*Size.*—1.5 mm wide and 3 mm long.

*Description.*—Glandular puberulent, ovoid.

*Color.*—Yellow 11C.

Flower:

*Type.*—Perfect.

*Shape.*—Campanulate.

*Size.*—4 mm deep and 7 mm wide.

*Petal description.*—5 in number, oblanceolate, 3 mm long and 1 mm wide, tip acuminate, base attenuate, margin entire, glabrous on both sides, White NN155D on both sides.

*Calyx description.*—3 mm deep and 5 mm wide, with 5 lobes, divided ½ way to the base, campanulate, glandular hairs on outside, glabrous inside, tip obtuse, margin entire, White 155C on both sides.

*Stamen description.*—5 in numbers, filaments 3 mm long, White NN155D, anthers sterile, less than 1 mm, Greyed Orange 164A.

*Pistil description.*—One central two beaked pistil, 4 mm long, White 155B.

*Fragrance.*—None.

*Lastingness.*—Each raceme blooms for about 2 weeks on the plant.

Fruit and seed: None

Disease and pest tolerance: No known resistances. Excellent disease tolerance to powdery mildew. All *Heucherella* are susceptible to root weevils.

I claim:

1. A new and distinct *Heucherella* plant as herein illustrated and described.

* * * * *

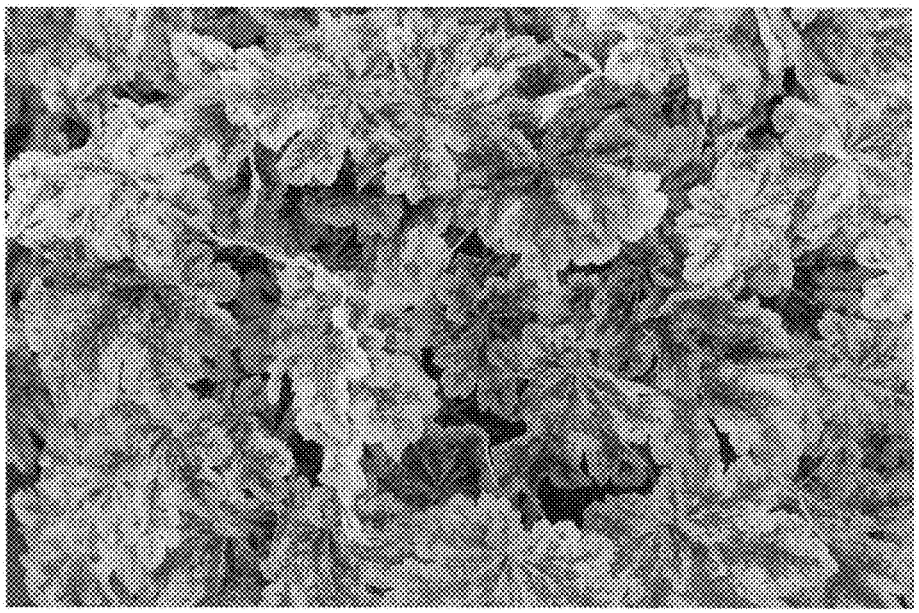

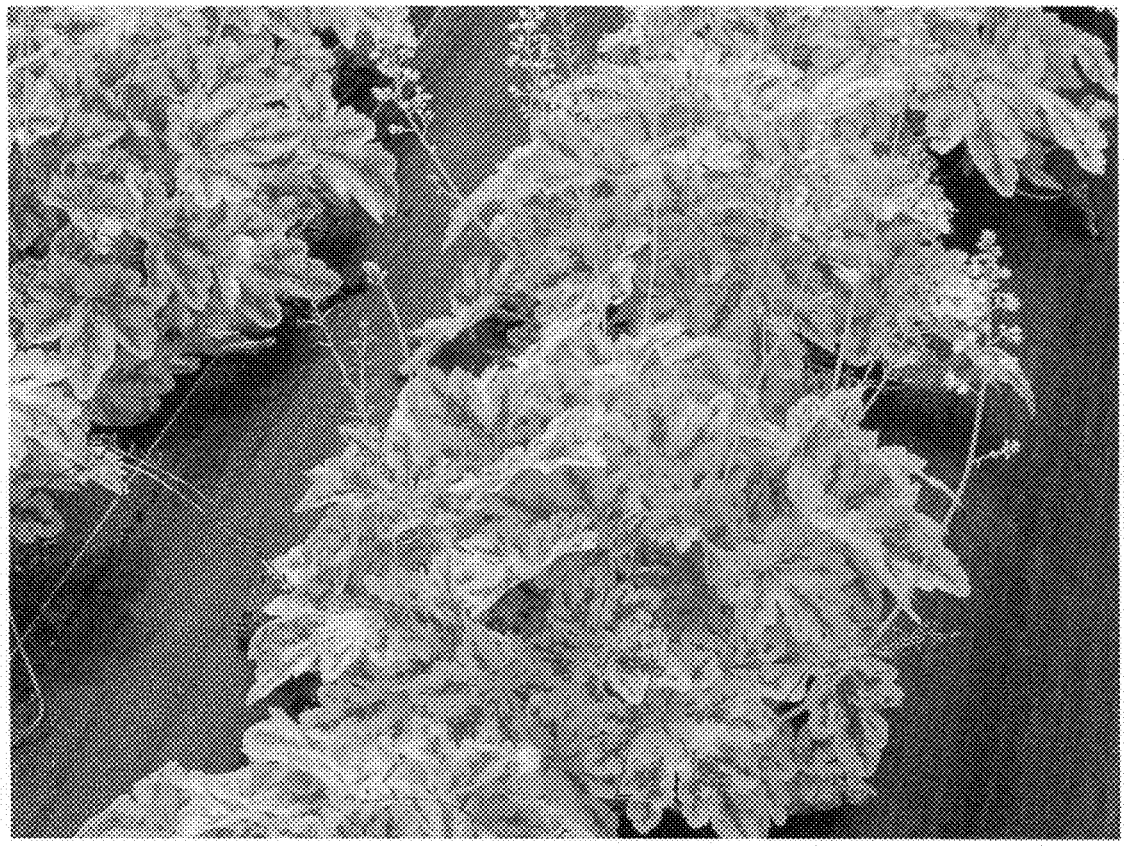
Figure 1 above. Figure 2 below.